United States Patent
Tomlinson et al.

(10) Patent No.: US 12,296,144 B2
(45) Date of Patent: May 13, 2025

(54) GUARD FOR ADAPTOR IN AN INTRAVENOUS LINE

(71) Applicant: Covalon Technologies Ltd., Mississauga (CA)

(72) Inventors: Sharon Tomlinson, Post Falls, ID (US); Mark Ford, Spokane, WA (US); Karl Frosh, Everett, WA (US); Gerry Arambula, Seattle, WA (US)

(73) Assignee: Covalon Technologies Ltd., Tukwila, WA (US)

( * ) Notice: Subject to any disclaimer, the term of this patent is extended or adjusted under 35 U.S.C. 154(b) by 0 days.

(21) Appl. No.: 17/096,628

(22) Filed: Nov. 12, 2020

(65) Prior Publication Data

US 2022/0062538 A1 Mar. 3, 2022

Related U.S. Application Data

(60) Provisional application No. 63/071,086, filed on Aug. 27, 2020.

(51) Int. Cl.
*A61M 5/158* (2006.01)
*A61B 5/00* (2006.01)
(Continued)

(52) U.S. Cl.
CPC .......... *A61M 5/158* (2013.01); *A61J 15/0026* (2013.01); *A61J 15/0053* (2013.01);
(Continued)

(58) Field of Classification Search
CPC ...... A61M 2039/0261; A61M 39/1011; A61M 2005/1586; A61M 2025/0246; A61M 2025/0253; A61M 2025/0266; A61M 2025/0273; A61M 2039/1016; A61M 39/101; A61M 25/02; A61M 5/5086; A61M 2039/0258; A61M 2039/1077; A61M 39/165; A61M 5/14248; A61B 5/6833; A61B 5/683; A61B 5/6832; A61J 15/0053

See application file for complete search history.

(56) References Cited

U.S. PATENT DOCUMENTS 4,490,141 A * 12/1984 Lacko .................. A61M 25/02
128/DIG. 26
4,704,177 A * 11/1987 Vaillancourt ....... A61M 39/165
156/289
(Continued)

*Primary Examiner* — William R Carpenter
*Assistant Examiner* — Robert F Allen
(74) *Attorney, Agent, or Firm* — Klarquist Sparkman, LLP

(57) ABSTRACT

There is provided a guard for an intravenous adaptor. The guard comprises a polymer sheet formed of a polymer film, the polymer sheet having left, right and middle portions; tear lines within the polymer sheet, located on either side of the central extent of the middle portion; a pull strip extending lengthwise, generally parallel to the central extent and positioned between the tear lines; and an adhesive applied to a periphery of the polymer sheet and over the ends of the pull strip, the tear lines penetrating through the adhesive. The left and right portions of the polymer sheet are arranged to be folded onto each other to form a folded polymer sheet adhered by the adhesive to define a pocket, which is openable by tearing the folded polymer sheet and adhesive along the tear lines.

18 Claims, 9 Drawing Sheets

(51) Int. Cl.
   *A61J 15/00* (2006.01)
   *A61M 25/02* (2006.01)
   *A61M 39/02* (2006.01)
   *A61M 39/10* (2006.01)

(52) U.S. Cl.
   CPC ........ *A61M 25/02* (2013.01); *A61M 39/0247* (2013.01); *A61M 39/1011* (2013.01); *A61B 5/683* (2013.01); *A61B 5/6832* (2013.01); *A61B 5/6833* (2013.01); *A61M 2005/1586* (2013.01); *A61M 2025/0246* (2013.01); *A61M 2025/0253* (2013.01); *A61M 2025/0266* (2013.01); *A61M 2025/0273* (2013.01); *A61M 2039/0258* (2013.01); *A61M 2039/0261* (2013.01); *A61M 2039/1016* (2013.01); *A61M 2039/1077* (2013.01); *A61M 2205/02* (2013.01)

(56) References Cited

U.S. PATENT DOCUMENTS

| | | | |
|---|---|---|---|
| 4,760,919 A | 8/1988 | Pereyra | |
| 4,863,432 A * | 9/1989 | Kvalo | A61M 25/02 604/177 |
| 5,163,554 A | 11/1992 | Lampropoulos et al. | |
| 5,219,336 A * | 6/1993 | Wilk | A61M 39/165 128/DIG. 26 |
| 5,392,918 A | 2/1995 | Harrison | |
| 5,417,668 A * | 5/1995 | Setzer | A61M 25/02 604/174 |
| 5,562,211 A | 10/1996 | Simons et al. | |
| 5,655,653 A | 8/1997 | Chester | |
| 6,651,813 B2 | 11/2003 | Vallans et al. | |
| 7,422,105 B2 | 9/2008 | Loyd et al. | |
| 7,524,307 B2 * | 4/2009 | Davis | A61M 25/02 604/174 |
| 7,910,632 B2 | 3/2011 | Cinader, Jr. et al. | |
| 8,157,770 B2 * | 4/2012 | Elwell | A61M 25/02 604/177 |
| 8,623,289 B2 | 1/2014 | Cesa et al. | |
| 9,629,779 B2 | 4/2017 | Grum-Schwensen et al. | |
| 2005/0023173 A1 * | 2/2005 | Paoletti | B65D 55/0854 215/230 |
| 2012/0109070 A1 * | 5/2012 | Elsamahy | A61M 25/02 604/179 |
| 2013/0267790 A1 * | 10/2013 | Pfuetzner | A61B 5/6832 600/300 |
| 2014/0039401 A1 * | 2/2014 | Kerr | A61M 25/02 604/180 |
| 2016/0206857 A1 * | 7/2016 | Mitchell | A61M 25/02 |
| 2016/0310665 A1 * | 10/2016 | Hwang | C09J 7/38 |
| 2017/0348477 A1 * | 12/2017 | Tomlinson | A61M 5/002 |
| 2018/0154118 A1 * | 6/2018 | Kyvik | A61M 25/02 |
| 2018/0353344 A1 * | 12/2018 | Locke | A61M 1/75 |

* cited by examiner

GUARD FOR ADAPTOR IN AN INTRAVENOUS LINE

CROSS-REFERENCE TO RELATED APPLICATIONS

This application claims benefit of, and priority from, U.S. provisional patent application No. 63/071,086, filed Aug. 27, 2020, the contents of which are incorporated herein by reference.

FIELD

This disclosure relates to guards to enclose and protect adaptors within an intravenous line, including protection from tampering by an unauthorized user and from contamination.

BACKGROUND

Vascular access devices (VADs) are routinely used during medical treatment to provide ongoing infusion of fluids and medication to a patient. VADs include various types of devices, some of which are used in a hospital setting for inpatients and others which are used for outpatient treatment that is provided on a continuing basis over a treatment period, for example chemotherapy. VADs are connected to an intravenous (IV) line, either central IV or peripheral IV, which will typically include one or more types of adaptors.

IV adaptors are found at the end of a section of IV tubing and serve to adapt the tubing for connection to another section of tubing, for merging lines supplying different medications or fluids, for injection or administration of medications or fluids, or for termination an IV line. Thus, IV adaptors can connect two or more pieces of IV tubing within an IV line, or can cap or terminate an IV line and thus connect to only a single piece of IV tubing.

Some IV adaptors allow access using a syringe or pump to administer medication or fluids, and therefore may provide an entry point into the patient's circulatory system and may be open to abuse by some patients as an easy way to take illicit intravenous drugs.

VADs are often left in place in a patient over a period of time, even for days or weeks, in order to provide fast and painless repeat or ongoing administration of the desired fluid or medication. As a result, the adaptors in the IV line that is inserted in a patient's body may be routinely exposed to environmental contaminants including fecal matter, saliva, and other bodily fluids, over the course of treatment. In addition, the proximity and accessibility of an IV adaptor in a VAD allows for patients to investigate and inspect the adaptor even out of curiosity, which can also lead to contamination.

Thus, there is a need to provide a mechanism that indicates tampering of an adaptor within an IV line while also protecting the adaptor from contamination.

SUMMARY

In one aspect, the present invention provides a guard for an intravenous adaptor, the guard comprising: a polymer sheet formed of a polymer film, the polymer sheet having left, right and middle portions; tear lines within the polymer sheet, located on either side of the central extent of the middle portion; a pull strip extending lengthwise, generally parallel to the central extent and positioned between the tear lines; and an adhesive applied to a periphery of the polymer sheet and over the ends of the pull strip, the tear lines penetrating through the adhesive; the left and right portions arranged to be folded onto each other to form a folded polymer sheet with the adhesive adhering the left and right portions to define a pocket to retain the intravenous adaptor; and the pull strip being positioned to allow the pocket to be opened by tearing the folded polymer sheet and the adhesive along the tear lines by urging the pull strip in a direction generally away from the pocket.

The guard may further comprise a release liner covering the adhesive to prevent the adhesive from adhering the left and right portions of the polymer sheet while the release liner is in place. In some embodiments, the release liner comprises a left section to cover the left portion and the left-most half of the middle portion of the polymer sheet and a right section to cover the right portion and the right-most half of the middle portion of the polymer sheet. In some embodiments, the release liner comprises a left section to cover the left-most part of the left portion of the polymer sheet and a right section to cover the right-most part of the right portion of the polymer sheet, the release liner further comprising a central section removable from the left and right sections, and covering the middle portion and the remaining parts of the left and right portions of the polymer sheet.

The pull strip of the guard may comprise a tab. In some embodiments, the tab may extend beyond the perimeter of the polymer sheet. In some embodiments, the peripheral edge of the polymer sheet includes notches in the left and right portions adjacent to the tear lines, the peripheral edge of the middle portion of the polymer sheet and the tab of the pull strip extending beyond the notches.

In another aspect, the present invention provides a guard for an intravenous adaptor, the guard comprising: a polymer sheet formed of a polymer film, the polymer sheet having left, right and middle portions; an adhesive applied to a periphery of the polymer sheet; and a release liner covering the adhesive to prevent the adhesive from adhering the left and right portions of the polymer sheet while the release liner is in place, the release liner comprising a left section to cover the left portion of the polymer sheet, a right section to cover the right portion of the polymer sheet, and a central section removable from the left and right sections and covering the middle portion of the polymer sheet; the left and right portions of the polymer sheet arranged to be folded onto each other to form a folded polymer sheet with the adhesive adhering the left and right portions to define a pocket to retain the intravenous injection port; and the guard being openable by urging the middle portion of the sheet in a direction generally away from the pocket.

In some embodiments, the left section of the release liner covers the left-most part of the left portion of the polymer sheet and the right section of the release liner covers the right-most part of the right portion of the polymer sheet, and the central section covers the middle portion and the remaining parts of the left and right portions of the polymer sheet.

The middle portion of the polymer sheet may further comprise a tab, the guard being openable by tearing the folded polymer sheet by pulling the tab in a direction generally away from the pocket.

The guard may also comprise tear lines within the polymer sheet, located on either side of the central extent of the middle portion, the tear lines penetrating the adhesive.

In the guard of the present invention, the left and right sections of the release liner may each comprise a flap.

As well, in some embodiments, the tear lines comprise a region of the polymer sheet that is thinner than the remainder of the polymer sheet not forming the tear lines. In some embodiments, the tear lines comprise perforations or microperforations.

The polymer film of the polymer sheet may comprise polyethylene. In some embodiments, the polymer film comprises low density polyethylene having greater tear strength in one of the machine direction and the transverse direction, and the tear lines generally align with the other of the machine direction and the transverse direction.

The adhesive may comprise a substrate coated with an adhesive coating, which may comprise a polyester film. The adhesive may comprise a pressure sensitive adhesive, for example, an acrylic pressure sensitive adhesive, a silicone pressure sensitive adhesive, or a rubber pressure sensitive adhesive.

The adhesive may comprise a first adhesive zone over the ends of pull strip and a portion of the periphery of the polymer sheet adjacent to the tear lines, and a second adhesive zone over the remainder of the periphery of the polymer sheet not included in the first adhesive zone, the adhesive in the first adhesive zone having a lower adhesive strength than the adhesive in the second zone In some embodiments, the polymer sheet is transparent, semi-transparent or translucent.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The figures illustrate, by way of example only, embodiments of the present invention, as follows.

DETAILED DESCRIPTION

Figure 1:
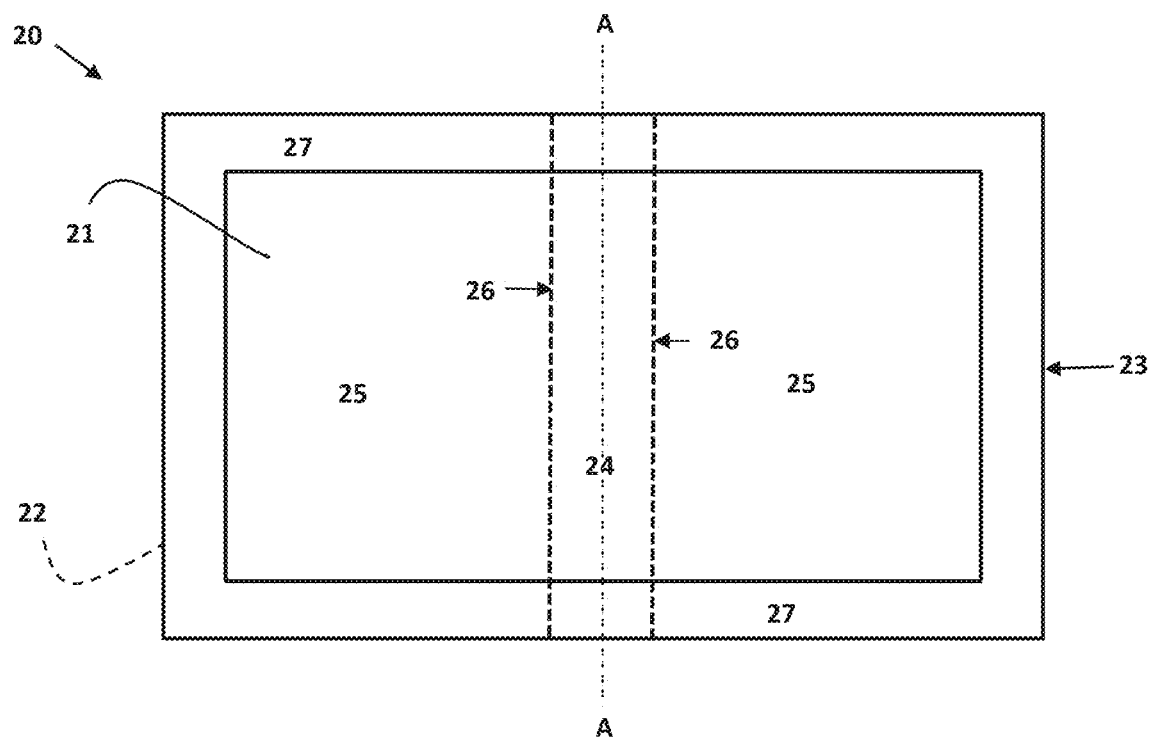
FIGS. 1 and 2 are top views of different embodiments of the polymer sheet.

There is provided a guard to enclose and protect an adaptor, also referred to herein as an IV adaptor, in an IV line that is connected to a patient, to thereby allow for monitoring of tampering with the adaptor and to reduce or prevent contamination of the adaptor and IV line.

As referenced herein, an IV adaptor, also referred to herein as an adaptor, is any device used to connect or terminate an IV line. Thus, IV adaptors are found at the end of a section of IV tubing that forms part of an IV line. Adaptors serve to connect sections of IV tubing within an IV line, to merge two or more sections of tubing that supply different medications or fluids, to allow access to the IV line for administration of medications or fluids, or to cap or terminate an IV line. IV adaptors may connect to two or more pieces of IV tubing, or may connect only with a single piece of IV tubing. IV adaptors include, for example, access ports, injection ports, connectors, needleless connectors, luer locks, caps and valves.

The guard encloses the junction points between the adaptor and any IV tubing connected to the adaptor, and may simultaneously enclose part or all of the adaptor.

An example guard includes a polymer sheet formed of a polymer film, having left, right and middle portions. The polymer sheet includes tear lines within the sheet, which are located on either side of the central extent of the middle portion of the sheet, and which separate the middle portion from the adjacent left and right portions.

The guard may further include a pull strip extending lengthwise along the middle portion of the polymer sheet, generally parallel to its central extent, from the periphery of the polymer sheet at one end of the central extent to the other.

The guard further comprises an adhesive applied to a periphery of the polymer sheet and over the ends of the pull strip if present where the pull strip crosses the periphery of the polymer sheet.

The tear lines extend through the adhesive, thus allowing the guard to be torn from one peripheral edge of the middle portion of the polymer sheet to the other, including through the adhesive, to separate the middle portion from the left and right portions of the polymer sheet upon opening of the guard.

The left and right portions of the polymer sheet are arranged to be folded onto each other to form a folded polymer sheet with the adhesive adhering the left and right portions to define a pocket to retain the intravenous adaptor. The adhesive over the pull strip also serves to form a seal around the circumference of any IV line that exits the guard, thus contributing to the overall seal of the guard.

Once enclosed around the adaptor, the guard can be opened by tearing the polymer sheet and adhesive along the tear lines, by urging the middle portion of the sheet in a direction generally away from the pocket. If the pull strip is present, this may be done by grasping the pull strip and applying a force to the pull strip, causing the guard to tear at the tear lines.

The guard may further include a release liner that is releasably adhered to the adhesive to prevent the adhesive from adhering the left and right portions of the polymer sheet while the release liner is in place, the release liner being removed during assembly of the guard around the adaptor.

The release liner may include a left section to cover the left portion of the polymer sheet and a right section to cover the right portion of the polymer sheet. The left and right section of the release liner may each include a flap, to assist with removal of the release liner during assembly of the guard around the adaptor.

The release liner may further include a central section that is removable from the left and right sections to facilitate deployment of the guard. The central section covers the pull strip which overlays the middle portion of the polymer sheet.

For example, the left section of the release liner may cover the left-most part of the left portion of the polymer sheet and the right section of the release liner may cover the right-most part of the right portion of the polymer sheet, and the central section covers the pull strip overlaying the middle portion and any remaining parts of the left and right portions of the polymer sheet not covered by the left and right sections of the release liner.

The polymer sheet may be transparent, semi-transparent or translucent. The adaptor thus may be visible through the guard, allowing for monitoring of the adaptor while the guard is in place.

The pull strip may be transparent, semi-transparent, translucent, or opaque. In some embodiments, a portion of the pull strip may be opaque or coloured while another portion is transparent, semi-transparent, or translucent, to allow for ease of visibility of the pull strip when opening the guard, yet still providing visibility of the area around the enclosed IV line.

When the guard is in place around the adaptor, the polymer sheet and the seal formed by the adhesive are waterproof, thus providing a protective barrier around the adaptor to reduce or prevent contamination of the adaptor during the course of IV treatment, including from biological contaminants such as fecal matter, saliva, and other bodily fluids, and from environmental contaminants such as pathogens or chemicals.

The polymer sheet is the main component of the guard that is likely to contact the patient's skin during use. The polymer sheet may be selected to be formed of a soft, pliable polymer film to reduce irritation of the patient's skin, and to assist with ease of assembly of the guard around the adaptor.

The polymer film forming the polymer sheet is selected to be strong and tear resistant, with the exception of the tear lines which are designed to tear upon application of a pre-determined force. The adhesive is chosen to form a strong seal between the adhesive and the polymer sheet and pull strip, and between two regions of the adhesive that contact each other when the guard is sealed around the adaptor. Thus, when in place, the guard provides a strong barrier to prevent tampering. Medical personnel may easily assess if the guard has been opened or has been otherwise damaged as a result of attempted tampering.

The guard is thus designed for quick, easy assembly around an IV adaptor, even when the user is wearing medical gloves. The release liner and the adhesive at the ends of the pull strip may allow for easy positioning of the adaptor upon removal of the central section, followed by efficient removal of the left and right sections of the liner while also sealing the adhesive around the circumference of the IV tubing and against itself. This design of the guard helps to avoid difficulty with the guard adhering to medical gloves during assembly around the adaptor.

The design of the guard also allows for quick removal of the guard when access to the adaptor is needed. The tear lines within the polymer sheet and through the adhesive coupled with the pull strip allow for rapid tearing of the polymer sheet, which destroys the guard. Destruction of the guard in this manner by an unauthorized person also serves as an indicator of tampering.

Thus, the guard includes a polymer sheet formed of a polymer film and defined by a peripheral edge, the polymer sheet having a first surface and a second surface.

The polymer sheet contains a middle portion across a mid-section of the polymer sheet, the middle portion extending from a portion of the peripheral edge of the polymer sheet, across the sheet to the opposing portion of the peripheral edge. The middle portion is defined by tear lines, which tear under application of a pre-determined force.

The tear lines of the polymer sheet separate the middle portion from left and right portions of the polymer sheet, one on each side of the middle portion.

Parameters of polymer films such as comonomer composition, branching degree and length, and manufacturing process can influence crystal orientation within the film and thus the mechanical properties of the film, including tear strength. Polymer films of various tear strength are available, and thus the polymer film used to form the polymer sheet may be selected to have good tear strength so as to resist tearing at locations other than the tear lines. Thus, the polymer film that forms the polymer sheet is substantially tear resistant, and thus does not tear easily except for along the tear lines, but which may deform without tearing when a force is applied to the guard at locations other than at the tear lines while the guard is in place around the adaptor.

Polymer films are available that have an increased tear strength in one direction as opposed to the cross direction. As will be appreciated, increased crystal orientation in a given direction within a polymer film can decrease tear strength in that direction. For example, a polymer film may have decreased tear strength in the machine direction as compared to the transverse direction, or vice versa, depending on crystal orientation within the polymer film.

Thus, the polymer film used to form the polymer sheet may be selected to have a difference in tear strength between the machine direction and the transverse direction of the polymer film. The polymer sheet may be designed from the polymer film such that the tear lines run in a direction of lower tear strength within the polymer film, assisting with the tearability along the tear lines while ensuring that the increased tear strength of the polymer sheet lies in a direction perpendicular to the tear lines. Such design takes advantage of internal directional strength of the polymer film to assist with the functionality of the guard.

This design of the polymer sheet in alignment with differing directional tear strength within the polymer film may also allow for the tear line, if perforated, to have smaller or fewer perforations or microperforations, thus improving leak resistance of the guard.

Alternatively, the polymer film used to make the polymer sheet may be selected to have similar or substantially the same tear strengths in both the machine direction and the transverse direction.

The polymer film is also transparent, semi-transparent, or translucent, to permit visualization and assessment of the adaptor and IV line while the guard is in place.

In addition, the polymer film is waterproof in order to repel body fluids and other contaminants with which the guard may come into contact during use.

The polymer film is also pliable and soft, to permit ease of use in terms of placing the guard around the IV adaptor. The pliability and softness may also impart low or no irritation for skin to the polymer film, as the second surface of the polymer sheet may contact a patient's skin when the guard is in place around the IV adaptor.

The polymer film may be any polymer film having the aforementioned attributes. For example, the polymer film may be a polyethylene film, including low density polyethylene films, such as linear low density polyethylene films.

The tear lines are regions in which the polymer film is weaker and thus is tearable along the tear lines upon application of a pre-determined force. The tear lines may be regions in which the polymer film is thinner and thus more susceptible to tearing. The tear lines may be lines of perforation or microperforation, to assist with tearing of the polymer sheet when the pre-determined force is applied.

As indicated above, the polymer film used to form the polymer sheet may be selected to have a tear strength in the direction of the tear lines such that if the tear lines are perforated, the tear lines may be designed to have a reduced or minimal number, size or spacing of perforations or microperforations.

The polymer sheet may be shaped so that the middle portion extends beyond the left and right portions at the peripheral edge, thus creating a tab within the polymer sheet.

The guard may in some embodiments include a pull strip which overlays the middle portion of the polymer sheet, placed over the sheet between the tear lines.

The pull strip may be adhered, annealed or laminated to the polymer sheet, or may simply be placed over the polymer sheet. Even when placed over the polymer sheet, the pull strip is secured in place within the guard by the adhesive portion of the guard, as described below.

In some embodiments, the pull strip extends at one or both ends beyond the peripheral edge of the polymer sheet to create a tab.

To create a tab with the end of the pull strip, the peripheral edge of the polymer sheet may be notched at the positions where the left and right portions meet the middle portion of the polymer sheet, on one or both ends of the middle portion, so that the end of the pull strip and also the peripheral edge of the middle portion of the polymer sheet extend beyond the notches in the left and right portions of the polymer sheet, thus creating a tab.

A notch created in the peripheral edge of the polymer sheet may also include the middle portion of the polymer sheet, such that the notch begins in the left or right portion, extends through the middle portion, and ends in the right or left portion of the polymer sheet. The end of the pull strip then extends beyond the peripheral edge of the notched middle section to create a tab.

When the guard is sealed in place around the IV adaptor, to remove the sealed guard from the IV adaptor, application of force on the pull strip when pulled by the tab toward the middle portion of the polymer sheet underlaying the pull strip, causes the polymer sheet to tear at the tear lines, thus opening the guard and allowing access to the adaptor.

The pull strip is therefore made of any resilient or flexible material that has sufficient strength to allow for pulling of the pull strip to tear the polymer sheet, and thus is more resistant to the force applied to open the guard than the tear lines within the polymer sheet and adhesive. For example the stiffener may be a polymeric material, including polyethylene, or may be metal, fabric or string.

The pull strip may be transparent, semi-transparent, translucent, or opaque. In some embodiments, a portion of the pull strip may be opaque or coloured while another portion is transparent, semi-transparent, or translucent.

For example, the tabs of the pull strip may be opaque or coloured, while the remainder of the pull strip that overlays the polymer sheet is transparent and uncoloured. In another example, the pull strip may be generally transparent and uncoloured, but may have an opaque or coloured patterned effect, such as dots or transverse stripes. In this way, the user may be able to easily locate the pull strip when the guard is in place around the adaptor, but may still be able to visualize the IV line through the pull strip, including to inspect the space between the pull strip and the IV line for fluid leak.

Overlaying a periphery of the polymer sheet and overlaying the end portions of the pull strip that lie over the periphery of the polymer sheet is an adhesive. The adhesive serves to seal and secure the sheet in place around the adaptor when the polymer sheet is fold over onto itself and about the adaptor, and to secure the pull strip to the surface of the polymer sheet.

The adhesive comprises an adhesive coating, which is selected to provide a strong bond between the left and right portions of the polymer sheet when folded together.

The width of periphery of the guard over which adhesive is applied is selected so that the adhesive will provide a sufficient bond around the periphery of the guard when the guard is in place around the IV adaptor, and also create a sufficient moisture barrier to prevent liquids from accessing the interior of the guard.

Thus, the adhesive bond formed by the adhesive is sufficiently strong to seal the guard when in place around the adaptor, to prevent contaminants from coming into contact with the adaptor.

The adhesive bond is also of sufficient strength such that the guard is destroyed if the adhesive bond is broken, in order to provide a clear indication that the IV adaptor has been accessed by removal of the guard.

The adhesive coating used for the adhesive may be any suitable adhesive coating having the aforementioned attributes. In some embodiments, the adhesive coating may comprise a pressure sensitive adhesive (PSA), such as an acrylic PSA, a silicone PSA, or a rubber PSA such as a natural or synthetic rubber PSA. PSAs do not require any solvent or heat to activate the adhesive bond, and the strength of the bond is determined by the amount of pressure applied to the adhesive.

In some embodiments, the adhesive comprises a substrate which is coated with the adhesive coating on opposing first and second surfaces of the substrate.

The inclusion of the coated substrate provides additional structure to the guard, by adding the weight of the substrate around the periphery of the guard and thus allowing for the use of a more flexible, thinner polymer film in the polymer sheet. The use of the coated substrate as the adhesive can therefore increase ease of handling of the guard during assembly around the adaptor.

As mentioned above, the adhesive overlays the periphery of the polymer sheet and also overlays the end portions of the pull strip that also overlay the periphery of middle portion of the polymer sheet. Thus, the coated first surface of the substrate faces and adheres to the polymer sheet in the periphery of the polymer sheet via the adhesive coating, as well as the end portions of the pull strip that overlay the periphery of the polymer sheet.

The adhesive, including the coated substrate if present, also includes tear lines through the adhesive. The tear lines may be lines of perforation or microperforation that penetrate through the adhesive, including through the coated substrate if present.

The tear lines assist with tearing of the guard, including tearing of the adhesive when the polymer sheet is torn, when the pre-determined force is applied to the pull strip. The tear lines of the adhesive align over the portion of tear lines of the polymer sheet over which the adhesive is positioned, such that tearing of the guard by application of force to the pull strip accomplishes tearing of the adhesive and the polymer sheet together. For ease of manufacture, the tear lines may be created once the polymer sheet, pull strip and adhesive are overlain, thus cutting through both the polymer sheet and the adhesive simultaneously.

The use of the coated substrate also allows for the use of different types of adhesive coating on the first and second surface of the coated substrate if desired. Thus, the adhesive coating may comprise a first adhesive coating on the first surface of the coated substrate and a second adhesive coating on the second coated surface of the coated substrate.

The first adhesive coating on the first surface of the coated substrate bonds the substrate to the surface of the polymer sheet and the ends of the pull strip around the periphery of the polymer sheet. Once the adhesive is in place, even before the guard is to be used, this bond does not need to be disrupted or opened. Thus, the first adhesive coating on the first surface may be selected to form a tight seal between the substrate and polymer film and the substrate and the pull strip, which seal cannot be broken without tearing of the polymer sheet. For example, the first adhesive coating may be a rubber adhesive, including a pressure sensitive rubber adhesive.

The second adhesive coating on the second surface of the coated substrate serves to adhere the left and right portions of the sheet together once the guard is assembled around the adaptor and IV tubing. The second adhesive coating on the second surface also adheres to the IV tubing of the IV line as it exits the guard on either side of the assembled guard, to help form the seal around the IV line while the guard is in place. Thus, the second adhesive coating on the second surface may be selected to adhere strongly to itself, but to adhere less strongly to IV tubing, so that the guard may be removed from the IV line and adaptor without difficulty. For example, the second adhesive coating may be an acrylic adhesive, including a pressure sensitive acrylic adhesive.

In some embodiments, the adhesive may comprise two or more adhesive zones, each adhesive zone comprising a different adhesive coating, which may be selected to have different adhesive properties, such as adhesive strength, and which may adhere differently to different surfaces.

For example, a first adhesive zone of the adhesive may encompass the portion of the adhesive that lies between the tear lines and overlays the end portions of the pull strip if present. The first adhesive zone of the adhesive may optionally extend beyond the tear lines to also overlay the portion of the periphery of polymer sheet that is immediately adjacent to the tear lines and which would also come in contact with the circumference of the IV tubing when the guard is in place. A second adhesive zone of the adhesive may encompass the remaining portion of the adhesive not encompassed by the first adhesive zone and overlay any remaining portions of the periphery of the polymer sheet not contained in the first adhesive zone.

The adhesive coating used in each zone may be selected to have different adhesive strength. In this way, the adhesive coating in the first adhesive zone may be selected to be of sufficient adhesive strength to seal the guard when in place around the adaptor while still being able to be removed from the IV tubing leaving minimal or no adhesive residue on the tubing. The adhesive coating in the second adhesive zone may be selected to have a higher adhesive strength as compared to the adhesive coating in the first adhesive zone and may adhere strongly to itself when the guard is assembled. For example, the adhesive coating in the first adhesive zone and the second adhesive zone may each be an acrylic adhesive, including a pressure sensitive acrylic adhesive, with the acrylic adhesive in the first adhesive zone having a lower peel strength than the acrylic adhesive in the second adhesive zone.

If the coated substrate is being used, the first adhesive coating on the first surface may be selected to be the same on the entire first surface, and may be selected to adhere strongly to the periphery of the polymer sheet and the ends of the pull strip if present. The second adhesive coating on the second surface may be selected to form zones with each zone having a different adhesive coating as described above. Thus, the second adhesive coating may comprise two or more types of adhesive coatings arranged in zones on the second surface of the coated substrate. For ease in manufacturing the guard, the coated substrate may be in several pieces, with the second surface of the pieces defining the zones.

The substrate may be any suitable substrate sufficient to carry the adhesive coating. For example, the substrate may be a flexible polymer tape, or may be a semi-rigid plastic layer. The substrate may be also transparent, semi-transparent or translucent, or may be opaque. For example, in some embodiments, the substrate may comprise a polyester film.

The choice of substrate for the coated substrate of the adhesive may depend on the choice of polymer film used to form the polymer sheet. For a thinner polymer sheet, a heavier, thicker, or more rigid substrate may be used, to assist with assembly of the guard in place around the adaptor and IV line.

The substrate is also chosen for tearability along the tear lines. Thus, while the substrate may be selected to provide structure to the guard as noted above, the substrate is also selected to tear easily upon application of the force on the pull strip.

During use, the guard is folded so that the left and right portions of the polymer sheet overlay each other, the adhesive adhering the polymer sheet in a folded configuration. The adhesive thus serves to adhere the periphery of the polymer sheet when the guard is in place around the adaptor, sealing the folded polymer sheet to form a pocket within the guard that holds the adaptor. The adhesive also adheres to any IV tubing exiting the guard at the location of the periphery of the middle portion of the polymer sheet, forming a seal around the exiting IV tubing. The seal formed by the adhesive thus functions to protect the IV adaptor from tampering and contamination, including from leakage of contaminating liquid into the guard.

The adhesive that overlays the pull strip on the periphery of the middle portion of the polymer sheet allows for IV tubing of an IV line to extend from the adaptor out of the guard when the guard is in place enclosing the adaptor while still maintaining the seal around the guard. The adhesive may be selected to adhere strongly to itself when the guard is in place but less strongly to the tubing, so that removal of the guard from the tubing does not disrupt the connections within the IV line.

Once the guard is sealed in place around the adaptor, the guard is opened by tearing the polymer sheet along the tear lines, resulting in destruction of the guard. A force is applied to the guard to urge the middle portion of the polymer sheet in a direction generally away from the pocket in which the adaptor is enclosed. This may be done by pulling on the tab of the pull strip.

As indicated above, the tear lines define the middle portion of the polymer sheet, traversing from the peripheral edge at one side of the polymer sheet, across the polymer sheet to the peripheral edge at the opposing side of the polymer sheet. The tear lines also penetrate through the adhesive where it crosses the tear lines in the periphery of the polymer sheet. Thus, tearing of the guard by pulling on the tab of the pull strip to remove the guard from around the IV adaptor results in tearing of the adhesive and the polymer sheet along the tear lines.

The guard may further include a release liner that releasably adheres to the surface of the adhesive on the polymer sheet, preventing the left and right portions of the polymer sheet from adhering while the release liner is in place. The release liner is removed during assembly of the guard around the adaptor, allowing the guard to be sealed upon folding of the polymer sheet.

As will be appreciated, the release liner is formed of a backing material. Release liner backing material is known, and is typically a coated paper or a polymer film that releasably adheres to an adhesive to prevent the adhesive from prematurely adhering before being placed in a desired position for adhesion. For example, the release liner may be a paper or polymer film coated with polymer or silicone.

The release liner may be a single sheet of the backing material. However, to assist with assembly of the guard around the adaptor, the release liner may be in two or more distinct pieces or sections, allowing for some portions of the adhesive to remain covered while other portions of the adhesive are revealed to assist with assembly.

In some embodiments, the release liner comprises a left and right section as distinct pieces of the release liner.

The left and right sections of the release liner may be of equal size, each covering half of the guard and meeting at or overlapping over the central line of the guard, thus each covering at least half of the adhesive around the periphery of the guard.

Alternatively, the left and right sections of the release liner may be of different sizes such that one of the left and right sections is a larger section that extends past the central line of the guard covering at least all of the right or left portion of the polymer sheet and more than half of the middle portion of the polymer sheet and the adhesive that overlays these portions of the sheet and pull strip. This larger section may even extend over part of the other of the left and right portions of the polymer sheet and associated adhesive. The other of the left and right sections of the release liner is then a smaller section that covers at least the remaining portion of the left or right portion of the sheet and associated adhesive not covered by the larger section of the release liner, but not extending over the central line of the guard. The larger section and the smaller section may overlap or may meet without overlapping.

With the release liner designed with a larger section and a smaller section of release liner, during assembly of the guard around the adaptor it is possible to peel back part of the larger section to reveal the pull strip over the central portion of the guard and associated adhesive. The adaptor can be positioned over the pull strip with the IV lines running along the pull strip and adhering to the adhesive applied at the end of the pull strip. The IV line can thus be anchored on the guard while the amount of adhesive exposed is minimized, in order to assist with assembly while the user assembling the guard in place is wearing gloves. Once the IV line is anchored, the rest of the larger and smaller sections of release liner can be removed as the guard is folded and adhered to itself via the adhesive around the periphery of the guard.

In other embodiments, in addition to the left and right sections, the release liner further comprises a separate piece that is a central section removable from the left and right sections. The left section of the release liner covers some or all of the left portion of the polymer sheet and associated adhesive and the right section of the release liner covers some or all of the right portion of the polymer sheet and associated adhesive, leaving the portion of the adhesive over the pull strip and middle portion of the polymer sheet, and optionally some of the adhesive in the left and right portions of the polymer sheet that is immediately adjacent to the middle portion of the polymer sheet, uncovered by the left and right sections of the release liner. The central section of the release liner covers the middle portion and may also cover any remaining uncovered parts of the left and right portions of the polymer sheet. The central section of the release liner may meet or may overlap with the left and right sections of the release liner.

In embodiments in which the release liner comprises left and right sections, even in embodiments that also include the central section of release liner, each of the left and right sections may have a flap that extends from an inner edge of the left or right section—i.e. the edge proximal to the middle portion—and which folds back over the respective left or right section. In some embodiments the flap may be long enough to extend beyond the peripheral edge of the polymer sheet when the release liner is in place releasably adhered to the adhesive. During use, the flaps can be used to remove the left and right sections of the release liner, thus reducing touching of the adhesive by the user.

During use, the release liner is removed and the polymer sheet is folded over onto itself and about an adaptor so that the adhesive seals the left and right portions of the polymer sheet to each other, forming a seal around the periphery of the guard with an interior pocket containing the adaptor. The release liner can be readily removed from the adhesive with minimal force, and can be put back in place, if necessary, provided that the polymer sheet has not yet been folded so that the adhesive forms the seal.

The guard thus is sealed about the adaptor, forming a pocket around the adaptor and the junction between the adaptor and any IV line connected to the adaptor, in which the first surface of the polymer sheet is in the interior of the pocket and is adjacent to the adaptor. The second surface of the polymer sheet forms the exterior surface of the guard when in place around the adaptor, with the IV line exiting the guard at the location of the pull strip which overlays the middle portion of the polymer sheet.

Generally, to assemble the guard around the adaptor, the guard is placed or held with second surface of the polymer sheet facing away from the adaptor.

If present, the release liner is pulled back or off to reveal the pull strip over top of the middle portion of the polymer sheet. In the case of the release liner having the left, right and central sections, the central section is removed to reveal the pull strip with adhesive at the ends of the pull strip in the region that the pull strip overlays the periphery of the polymer sheet. The left and right sections of the release liner may be left in place while the adaptor and IV line is positioned, to assist with assembly by preventing the user's gloves or skin from coming into contact with the adhesive.

The adaptor is placed in position over the pull strip with the IV line extending from the adaptor out from the guard at the peripheral edge of the polymer sheet in the location of the middle portion, over top of the ends of the pull strip, such that the junction between the adaptor and the IV tubing is within the area of the polymer sheet defined by the adhesive. The adaptor may be connected in line in an IV line, such that there are two or more sections of IV tubing connected to the adaptor, for example one section of IV tubing between a fluid reservoir and the adaptor and another section of IV tubing between the adaptor and the patient. In such an embodiment, sections of IV line may exit at each side of the guard. In other embodiments, the adaptor may be connected to only one section of IV line, connected to the patient, for example where the adaptor is an injection port at the end of an IV line.

The adhesive over the ends of the pull strip allows for anchoring of the adaptor in place during assembly by adhering to the IV line that exits the guard while remaining release liner is removed and the guard is sealed.

The adhesive over the ends of the pull strip also extends the seal of the guard around exiting IV line, to help improve the protection of the adaptor within the sealed guard. That is, the adhesive is located to so that as the polymer sheet curves around the exiting tubing of the IV line, the adhesive adheres to the circumference of the tubing, and then adheres to itself as the left and right portions of the polymer sheet meet over top of the tubing. Thus, during assembly of the guard, a tight seal can be formed even around exiting IV line.

Once the adaptor is in place over the pull strip and the IV line is anchored at one or both ends of the pull strip, any remaining release liner is removed and the guard is simultaneously sealed. For example, if left and right sections of release liner are present and comprise a flap, the user may hold the guard with anchored IV lines in one hand and grasp one or both flaps with the other hand, pulling on the flaps to peel off the left and right sections of the release liner. The seal around the circumference of the tubing can be secured and the left and right portions of the polymer sheet can then be sealed to each other, thus forming the sealed pocket containing the adaptor.

Once the guard is in place around the adaptor, the guard exhibits a strong seal provided by the adhesive sealing the left and right portions of the polymer sheet to each other and the adhesive sealing around the circumference of the IV line where it exits the guard at the position of the pull strip. The polymer sheet, as well as the seal provided by the adhesive serve to help reduce contaminants from entering the adaptor.

Due to the strength of the polymer sheet and the adhesive seal, once the guard is in place around the adaptor, the guard resists opening and tearing, except for along the tear lines. To re-access the adaptor, the guard is torn by applying a force sufficient to tear the polymer sheet at the tear lines, in a direction generally away from the pocket, by grasping the polymer sheet, the pull strip, or a tab if present.

As indicated above, the adhesive coating that forms the seal between the left and right portions of the polymer sheet and around the IV tubing may be selected so that the adhesive adheres strongly to the coated substrate or polymer sheet, to itself, and to the pull strip, but less strongly to the polymer of the tubing.

To facilitate the difference in adhesion of the guard to itself and to the IV tubing, the adhesive may be applied in the first and second adhesive zones described above, with the adhesive coating in the first adhesive zone selected to form a bond with the IV tubing yet leave minimal or no adhesive residue upon removal of the guard. The adhesive coating in the second adhesive zone may be selected to form a strong bond when adhered to itself, and may be selected to have a higher adhesive strength or higher peel strength than the adhesive coating in the first adhesive zone.

This allows for removal of the guard with minimal or no disruption of the IV line. Medical tubing is widely commercially available and may be composed of polyurethane, polyolefin, PVC, PTFE, or PEEK.

Opening the guard by pulling on the tab of the pull strip is quick and efficient, and also results in destruction of the guard. Thus, it is readily apparent to medical personnel if the adaptor has been accessed by destruction of the guard.

Certain embodiments of the guard are described in more detail below, with reference to the accompanying figures.

Figure 2:
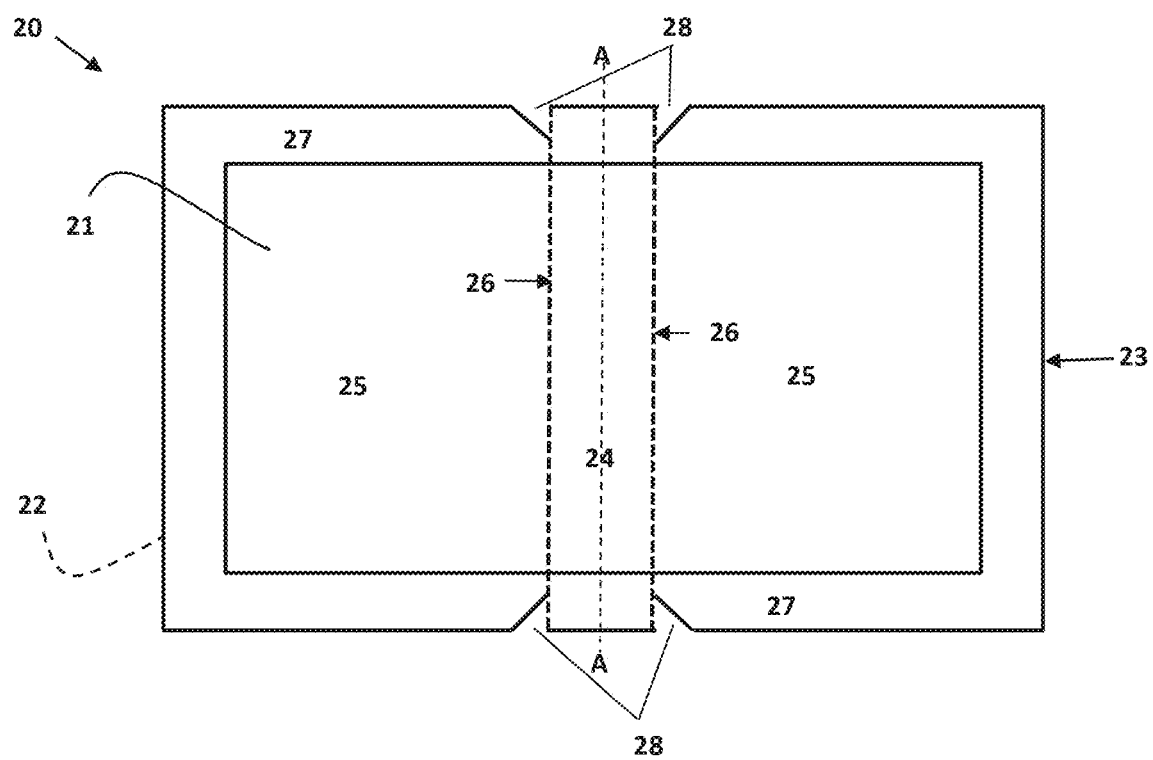

An example guard 10 comprises a polymer sheet 20 as depicted in FIGS. 1 and 2. Polymer sheet 20 has a first surface 21, an opposing second surface 22, and is defined by a peripheral edge 23.

Polymer sheet 20 has a middle portion 24, that runs from one part of peripheral edge 23 across first surface 21 to a second opposing part of the peripheral edge 23. Middle portion 24 is positioned about a central axis A, which defines a centre line across the plane of the polymer sheet 20.

On either side of the middle portion 24, are left and right portions 25 of the polymer sheet 20. The two left and right portions 25 are separated from the middle portion 24 by tear lines 26.

The first surface 21 has a peripheral portion 27 around the outer edge of the two left and right portions 25, the peripheral portion being defined on the outer edge by peripheral edge 23. The peripheral portion runs around the outer edge region of the first surface 21, including around the outer edge region of the first surface 21 defined by the two left and right portions 25, and across the outer edge regions defined by the middle portion 24 that are adjacent to the peripheral edge 23.

As seen in FIG. 2, in some embodiments peripheral portion 27 has notches 28 that reduce the width of the peripheral portion in a region immediately adjacent to the middle portion.

Polymer sheet 20 is sized so that when folded in half about the central axis A, polymer sheet 20 forms a pocket sufficient to fully surround and enclose an adaptor within the region of the left and right portions that is not encompassed by peripheral portion 27.

Although depicted in FIGS. 1 and 2 as generally rectangular, polymer sheet 20 may be any shape. Regardless of shape, polymer sheet 20 typically has mirror symmetry reflected across central axis A. Thus, when folded along central axis A, the peripheral edge 23 of a first half of the polymer sheet 20 meets and aligns with the peripheral edge 23 of a mirror image second half of the polymer sheet 20.

Guard 10 also comprises a pull strip 40 having longitudinal edges 41.

Figure 3:
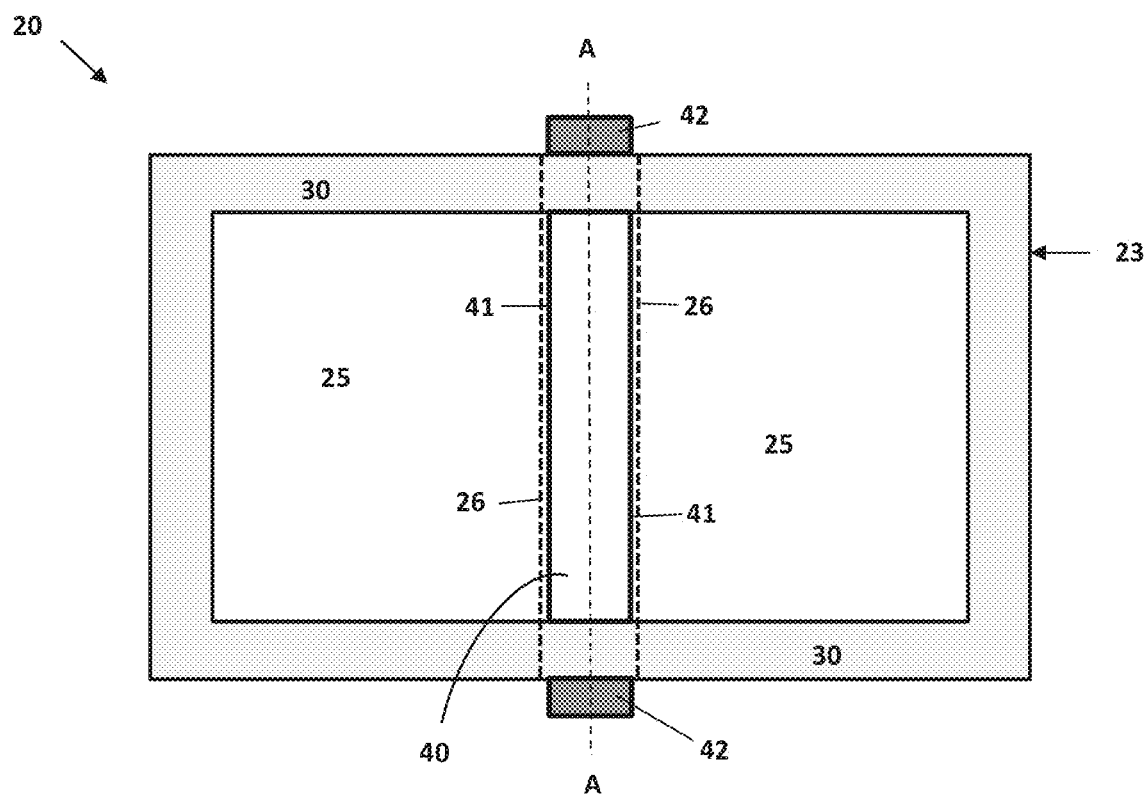
FIGS. 3 and 4 are top views of a polymer sheet with a pull strip overlaying the middle portion of the polymer sheet and an adhesive overlaying the peripheral portion of the polymer sheet and the pull strip.
Figure 4:
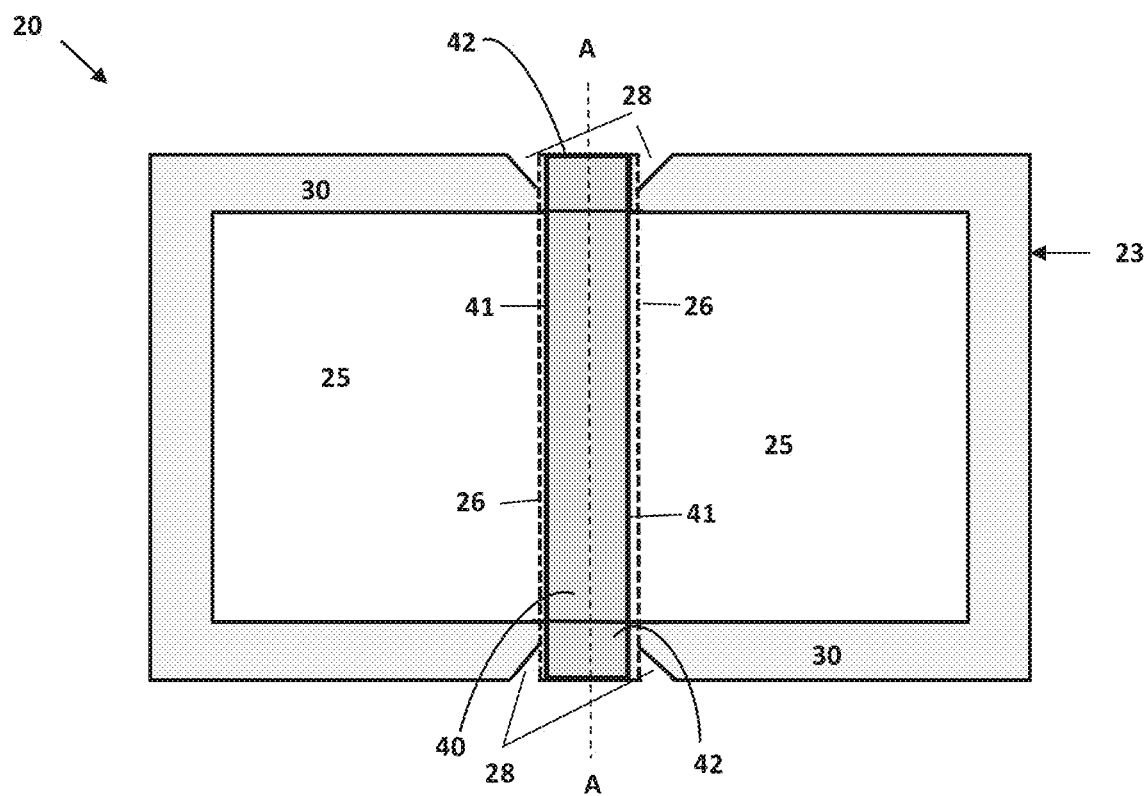

As shown in FIGS. 3 and 4, the pull strip 40 overlays middle portion 24 of the polymer sheet 20, with the longitudinal edges 41 positioned overtop of or adjacent to the tear lines 26, such that when the guard 10 is secured in place around the adaptor and a pre-determined force is applied to pull strip 40 in a direction toward the first surface 21, the longitudinal edges 41 of the pull strip 40 push against or adjacent to tear lines 26, tearing polymer sheet 20 along the tear lines 26.

As seen in FIGS. 3 and 4, adhesive 30 overlays the peripheral portion 27 of polymer sheet 20, and also overlays pull strip 40 in the region of the pull strip that lies overtop of the peripheral portion 27. Tear lines 26 also perforate through the adhesive 30.

In FIG. 3, the pull strip 40 is depicted as including a tab 42 at one or both ends that extends beyond the portion of the peripheral edge 23 defining the middle portion 24.

In FIG. 4, peripheral edge 23 of polymer sheet 20 has notches 28, and thus pull strip 40 extends beyond peripheral edge 23 in the region of notches 28 to create tabs 42.

Figure 5:
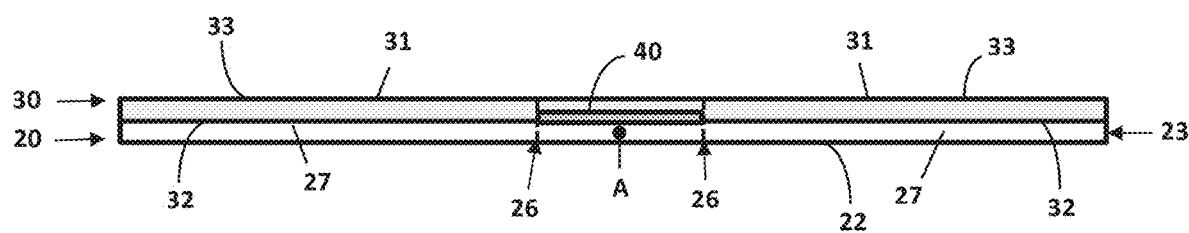
FIG. 5 is a cross sectional views of one embodiment of the polymer sheet and adhered adhesive, through the peripheral portion of the polymer sheet.

As depicted in FIG. 5, adhesive 30 comprises a substrate 31, having a first coated substrate surface 32 and a second coated substrate surface 33, each coated with an adhesive coating.

Adhesive 30 is layered on polymer sheet 20 in peripheral portion 27 of polymer sheet 20 and also over the portions of pull strip 40 that lie overtop of peripheral portion 27. Specifically, the first coated substrate surface 32 contacts the first surface 21 of the polymer sheet 20 in the peripheral portion 27 and pull strip 40, thus adhering both the adhesive 30 and the pull strip 40 to the polymer sheet 20.

The placement of adhesive 30 in peripheral portion 27 provides support to guard 10 due to the presence of substrate 31, which provides some stiffness to the polymer sheet 20 during assembly of the guard 10 around the adaptor and while the guard 10 is in place.

Figure 6:
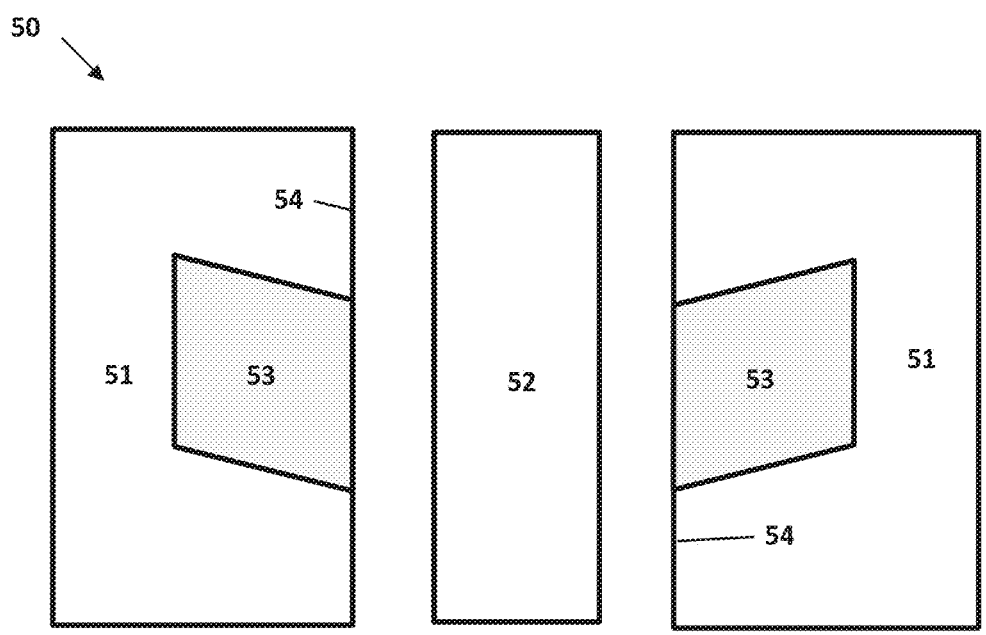
FIG. 6 depicts a three-part release liner of the invention.
Figure 7:
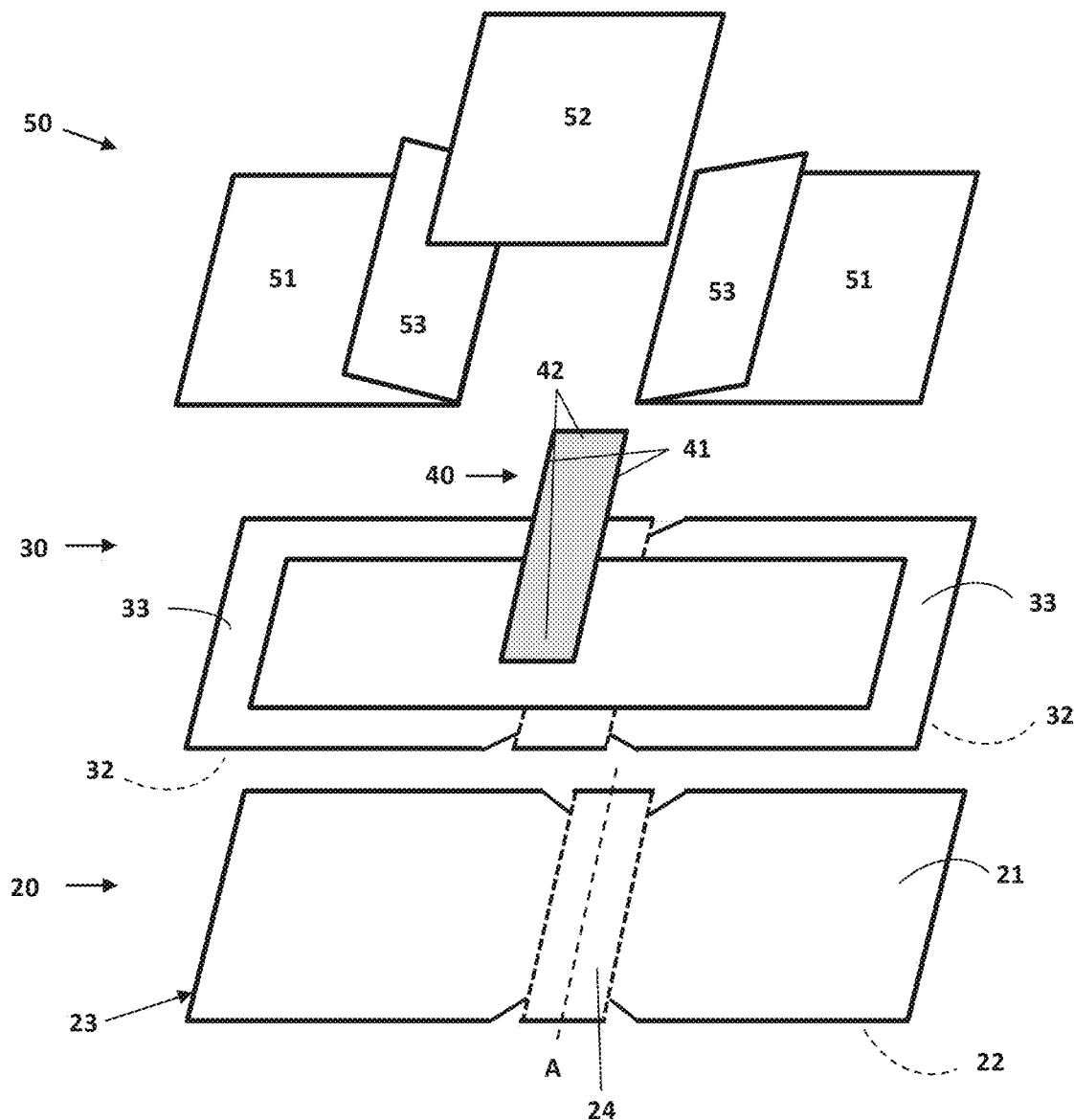
FIGS. 7 and 8 are exploded views of embodiment guards of the invention.
Figure 8:
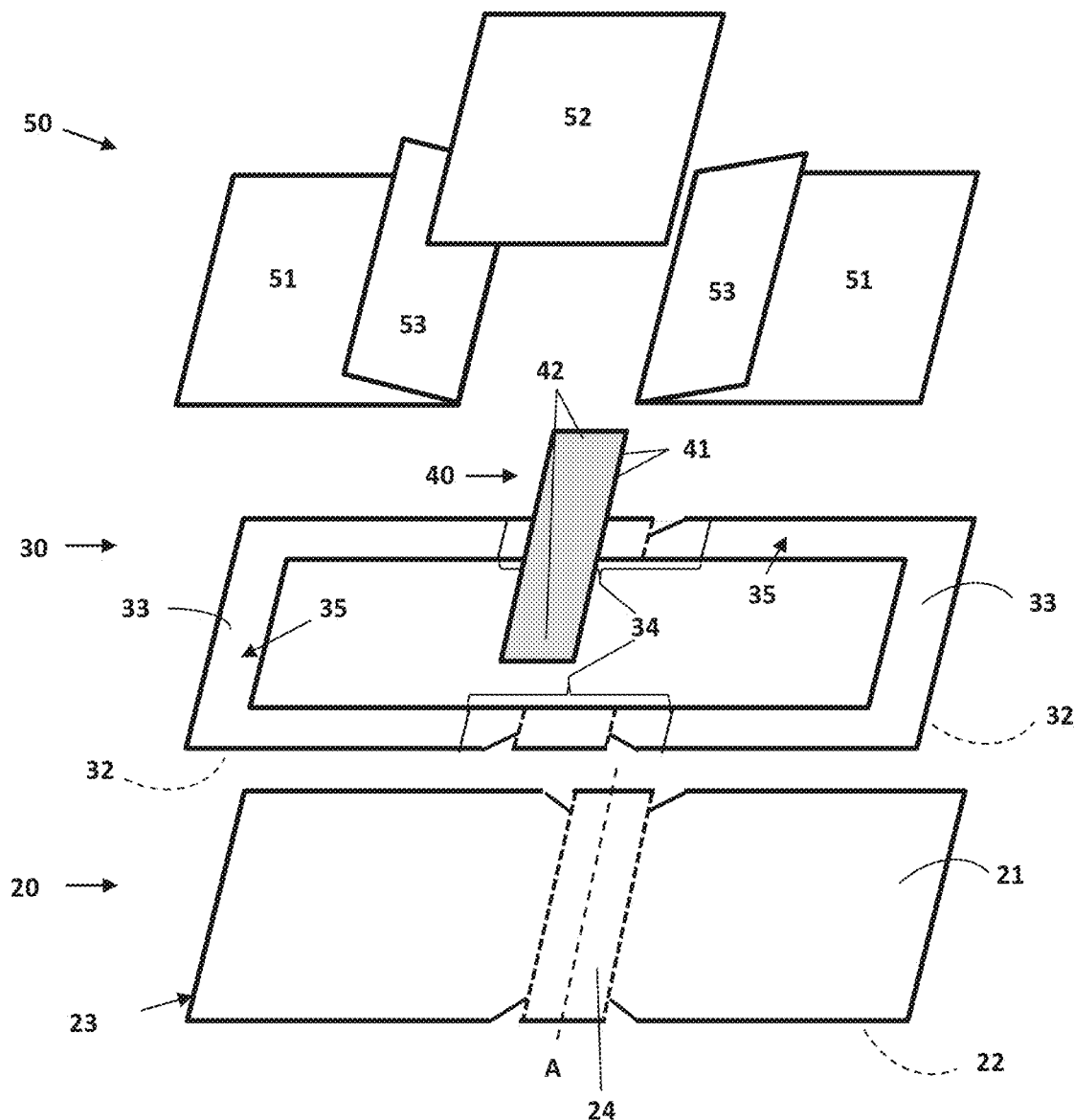

Guard 10 also comprises a release liner 50 having left and right sections 51 and a central section 52, as depicted in FIGS. 6 to 8.

Each of the left and right sections 51 is sized and shaped to cover a portion of respective left and right portions 25, while leaving a portion of the left or right portion 25 that is immediately adjacent to the middle portion 24 uncovered. The left and right sections 51 of release liner 50 thus releasably adhere to the second coated substrate surface 33 of the portions of the adhesive 30 covered by the left and right sections 51.

As depicted in FIGS. 6 to 8, each left and right section 51 has a flap 53 that extends from an inner edge 54 and extending over the surface of the left or right section 51. Flap 53 may extend from the entire length of inner edge 54, as shown in FIGS. 7 and 8, or may extend from only a portion of inner edge 54, for example from the centre region of inner edge 54, as shown in FIG. 6.

Central section 52 is sized and shaped to cover the middle portion 24 with the pull strip 40 layered thereon and the remaining portions of left and right portions 25 that are not covered by the left and right sections 51. The central section 52 thus releasably adheres to the second coated substrate surface 33 of the portions of the adhesive 30 covered by the central section 52. When in place, the central section 52 may overlap with left and right sections 51. If so, in the overlapping sections, the central section 52 is positioned overtop of left and right sections 51.

During use, guard 10 is placed or held with second surface 22 facing outward or downward, and with the central section 52 and the left and right sections 51 facing upward or in the direction of the adaptor that is to be placed.

Central section 52 is removed and discarded, and the adaptor is placed in position with the IV line extending from the adaptor out from the guard at the position where the pull strip 40 sits at the peripheral edge 23 of the middle portion 24, and is adhered to the portion of adhesive 30 that lies overtop of the pull strip 40.

As can be seen in FIG. 8, the adhesive may be arranged in a first adhesive zone 34 and a second adhesive zone 35, and may exhibit different adhesive strengths, with first adhesive zone 34 having a lower adhesive strength as compared to that of second adhesive zone 35.

Once the adaptor is placed with the IV line aligned along pull strip 40, the left and right sections 51 can be grasped by flaps 53. If desired, for ease of removal this may be done with a single hand grasping both flaps 53, while the user's second hand supports the guard 10 by holding the guard at second surface 22 of the polymer sheet 20.

Figure 9:
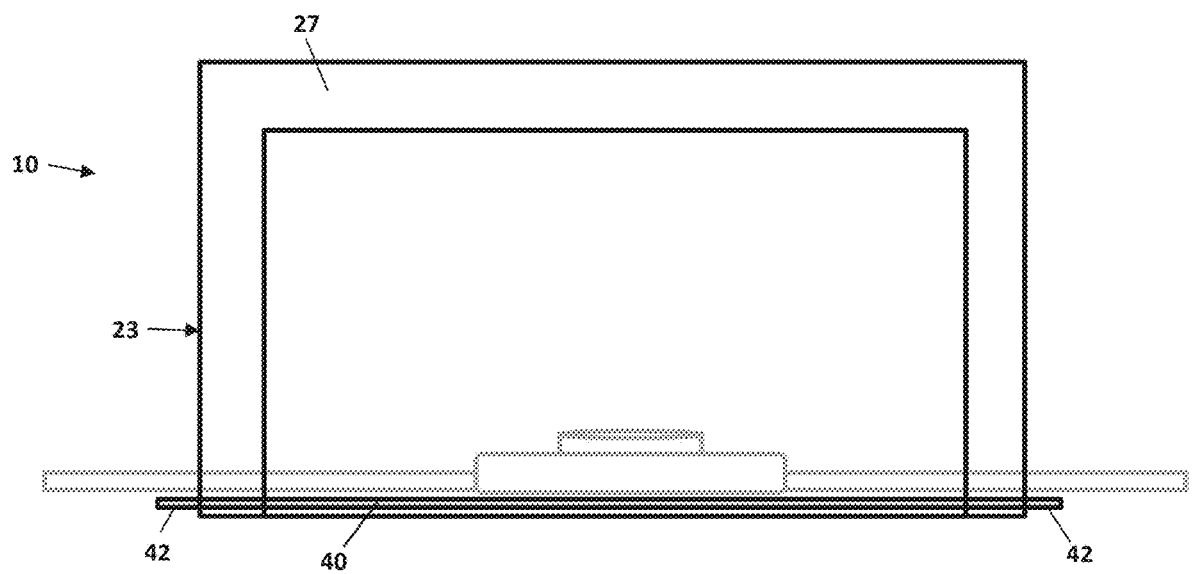
FIG. 9 depicts an embodiment of the guard sealed around an adaptor.

As the left and right sections 51 are removed from the guard 10, the polymer sheet 20 is folded over onto itself along the central axis A, bringing the two sections of the second coated substrate surface 33 into contact with each other. The two portions of second coated substrate surfaces 33 are thus adhered together, sealing the peripheral portion 27 of the guard 10, with the adaptor enclosed within the guard 10, as seen in FIG. 9.

To re-access the adaptor, the guard 10 is torn by grasping the tab 42 and applying sufficient force to tear the polymer sheet 20 at the tear lines 26.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. As used in this specification and the appended claims, all ranges or lists as given are intended to convey any intermediate value or range or any sublist contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A guard for an intravenous adaptor, the guard comprising:
    a polymer sheet formed of a polymer film, the polymer sheet having left, right and middle portions;
    tear lines within the polymer sheet, located on either side of a central extent of the middle portion;
    a pull strip that overlays the middle portion of the polymer sheet, extending lengthwise along, and generally parallel to, the central extent of the middle portion, from a periphery of the polymer sheet at one end of the central extent to the periphery of the polymer sheet at an opposing end of the central extent, the pull strip positioned between the tear lines; and
    an adhesive applied to the periphery of the polymer sheet and over ends of the pull strip where the pull strip crosses the periphery of the polymer sheet, the tear lines penetrating through the adhesive;
    the middle portion positioned about a central axis that defines a center line across the polymer sheet, the left and right portions located on either side of the middle portion, separated from the middle portion by the tear lines, the left and right portions arranged to be folded onto each other when the polymer sheet is folded about the central axis to form a folded polymer sheet, with the adhesive around a portion of the periphery on the right portion of the polymer sheet adhering to the adhesive around a portion of the periphery on the left portion of the polymer sheet to thereby form a sealed periphery of the folded polymer sheet to thus define a pocket to retain the intravenous adaptor, the pocket bounded by the sealed periphery and a folded edge along the central axis of the folded polymer sheet and enclosed by the left and right portions of the polymer sheet; and
    the pull strip being positioned over the middle portion of the polymer sheet to allow the pocket to be opened by tearing the folded polymer sheet and the adhesive along the tear lines by urging the pull strip and the middle portion in a direction generally away from the pocket to thereby result in destruction of the guard.

2. The guard of claim 1, further comprising:
a release liner covering the adhesive to prevent the adhesive from adhering the left and right portions of the polymer sheet while the release liner is in place.

3. The guard of claim 2, wherein the release liner comprises a left section to cover the left portion and a left-most half of the middle portion of the polymer sheet and a right section to cover the right portion and a right-most half of the middle portion of the polymer sheet.

4. The guard of claim 2, wherein the release liner comprises a left section to cover a left-most part of the left portion of the polymer sheet and a right section to cover a right-most part of the right portion of the polymer sheet, the release liner further comprising a central section removable from the left and right sections, and covering the middle portion and the remaining parts of the left and right portions of the polymer sheet.

5. The guard of claim 4, where the left and right sections of the release liner each comprise a flap.

6. The guard of claim 1, wherein the pull strip comprises a tab.

7. The guard of claim 6 wherein the tab extends beyond a perimeter of the polymer sheet.

8. The guard of claim 6, wherein a peripheral edge of the polymer sheet includes notches in the left and right portions adjacent to the tear lines, and wherein a peripheral edge of the middle portion of the polymer sheet and the tab of the pull strip extend beyond the notches.

9. The guard of claim 1, wherein the tear lines comprise a region of the polymer sheet that is thinner than the remainder of the polymer sheet not forming the tear lines.

10. The guard of claim 1, wherein the tear lines comprise perforations or microperforations.

11. The guard of claim 1, wherein the polymer film comprises low density polyethylene having greater tear strength in one of a machine direction and a transverse direction, and the tear lines generally align with the other of the machine direction and the transverse direction.

12. The guard of claim 1, wherein the polymer film comprises polyethylene.

13. The guard of claim 1, wherein the adhesive comprises a substrate coated with an adhesive coating.

14. The guard of claim 13, wherein the substrate comprises a polyester film.

15. The guard of claim 1, wherein the adhesive comprises a pressure sensitive adhesive.

16. The guard of claim 15, wherein the pressure sensitive adhesive comprises an acrylic pressure sensitive adhesive, a silicone pressure sensitive adhesive, or a rubber pressure sensitive adhesive.

17. The guard of claim 1, wherein the adhesive comprises a first adhesive zone over the ends of the pull strip and a portion of the periphery of the polymer sheet adjacent to the tear lines, and a second adhesive zone over the remainder of the periphery of the polymer sheet not included in the first adhesive zone, the adhesive in the first adhesive zone having a lower adhesive strength than the adhesive in the second zone.

18. The guard of claim 1, wherein the polymer sheet is transparent, semi-transparent or translucent.

* * * * *